United States Patent [19]

Monson

[11] 4,377,343
[45] Mar. 22, 1983

[54] DUAL-BEAM SKIN FRICTION INTERFEROMETER

[75] Inventor: Daryl J. Monson, Cupertino, Calif.

[73] Assignee: The United States of America as represented by the Administrator of the National Aeronautics and Space Administration, Washington, D.C.

[21] Appl. No.: 282,192

[22] Filed: Jul. 10, 1981

[51] Int. Cl.³ ..................... G01B 9/02; G01B 11/06
[52] U.S. Cl. ........................................ 356/357; 73/147
[58] Field of Search ................. 356/351, 352, 357; 73/147

[56] References Cited

U.S. PATENT DOCUMENTS 4,147,435  4/1979  Habegger .................. 356/357

OTHER PUBLICATIONS

Tanner et al., "A Study of the Motion of Oil Films on Surfaces in Air Flow ... ", *J. Phys. E: Sci. Instru.*, vol. 9, pp. 194–202, 1976.
Tanner, "A Skin Friction Meter, Using the Viscosity Balance Principle ... ", *J. Phys. E: Sci. Instru.*, vol. 10, pp. 278–284, 1977.
Tanner, "A Comparison of the Viscosity Balance and Preston Tube Methods ... ", *J. Phys. E: Sci. Instru.*, vol. 10, pp. 627–632, 1977.

Primary Examiner—John K. Corbin
Assistant Examiner—Matthew W. Koren
Attorney, Agent, or Firm—Darrell G. Brekke; John R. Manning; Robert D. Marchant

[57] ABSTRACT

A portable dual-laser-beam interferometer is described that nonintrusively measures skin friction by monitoring the thickness change of an oil film at two locations while said oil film is subjected to shear stress. An interferometer flat is utilized to develop the two beams. Light detectors sense the beam reflections from the oil film and the surface thereunder. The signals from the detectors are recorded so that the number of interference fringes produced over a given time span may be counted.

8 Claims, 4 Drawing Figures

DUAL-BEAM SKIN FRICTION INTERFEROMETER

DESCRIPTION

Origin of the Invention

The invention described herein was made by an employee of the U.S. Government and may be manufactured and used by or for the Government for governmental purposes without the payment of any royalties thereon or therefor.

BACKGROUND ART

1. Field of the Invention

This invention relates to a novel interferometric apparatus for accurately and nonintrusively measuring surface skin friction on a model or a body in an air flow and for accurately measuring the viscosity of the oil used for the skin friction measurement.

2. Description of the Prior Art

There are numerous devices in common usage to measure skin friction. The commonest are Preston tubes, surface thin-film heat-transfer gages and floating-element balances which are used to make mean-velocity profile boundary layer surveys for use in conjunction with the Clauser chart. These devices are described and discussed in detail in "An Outline of the Techniques for the Measurement of Skin Friction in Turbulent Boundary Layers," K. G. Winter, *Progress in the Aerospace Sciences*, Vol. 18, Pergamon Press, Great Britain 1977, pp. 1–57. Except for the floating-element balance, all of the aforementioned devices measure skin friction indirectly since they are based on the wall similarity in turbulent boundary layers. The floating-element balance does measure skin friction directly; however, it has critical gap and alignment problems, especially when subjected to a pressure gradient. Further, these balances are very delicate and expensive. All of the mentioned instruments are undesirable in that they must be installed in the surface being measured or they must intrude in the flow.

Tanner has described a skin friction instrument that overcomes some of the limitations of the previously noted devices. "A Study of the Motion of Oil Films on Surfaces in Air Flow, With Application to the Measurement of Skin Friction," L. H. Tanner and L. G. Blows, *Journal of Physics E: Scientific Instruments*, Vol. 9, 1976, pp. 194–202; "A Skin Friction Meter, Using the Viscosity Balance Principle, Suitable for Use with Flat or Curved Metal Surfaces," L. H. Tanner, *Journal of Physics E: Scientific Instruments*, Vol. 10, 1977, pp. 278–284; "A Comparison of the Viscosity Balance and Preston Tube Methods of Skin Friction Measurement," L. H. Tanner, *Journal of Physics E: Scientific Instruments*, Vol. 10, 1979, pp. 627–632. The instrument uses a laser to interferometrically measure the thickness of an oil film flowing on a surface subject to skin friction. The thickness measurements are, in turn, used with a theory that describes the flow of the oil to compute ski friction. Although it is a direct method and does not require calibration in a known flow, its use has not been widely adopted for measuring skin friction because of several shortcomings. Tanner employs a first layer beam to measure oil thickness. Tanner's oil-flow theory requires a very accurate determination of the distance between the oil film leading edge and the laser beam focal point. Tanner employs a second laser beam (with fixed spacing from the first beam) as a "spotter beam" and visually positions the beam at the leading edge of the oil before a test. This manual distance measurement method is inconvenient at best and may be impossible in many wind tunnels because of visibility limitations. The measurement is also prone to error because of the subjective nature of visually locating the oil leading edge, and because the oil applied to the surface is not confined, the leading edge can significantly move between the time the spotter beam is positioned on the oil leading edge and the time the wind tunnel is started. [When Tanner encountered problems caused by wind tunnel vibrations in the two-beam measurement instrument, he tried an alternate apparatus and that also failed to obviate the aforementioned problems. The second embodiment utilized a single laser beam. Tanner initially visually aimed the beam at the oil leading edge and then moved the beam downstream with a slip gauge. A micrometer was used to measure the spot displacement.] Tanner's skin friction process requires that the total oil flow time be accurately known and he provides no way of measuring it. Tanner merely assumes that the oil flow commences when the wind tunnel is started. This assumption is subject to unknown error because of prerun oil flow, tunnel starting transients, and initial surface waves which form on the oil. These limitations have the cumulative effect of making Tanner's skin friction measurement method impractical for wind tunnel testing.

SUMMARY OF THE INVENTION

According to this invention some droplets of oil are dispensed on the surface of the model or body to be wind tunnel tested. As air flow in the wind tunnel passes over the oil film created by the droplets and changes its thickness, two light beams a known distance apart are focused on the oil film. One beam is situated upstream of the other beam. The two beams are produced by a laser beam aimed at an angled interference flat. The two beams reflected from the flat pass through a window in the wind tunnel and impinge on the oil film. A telescope permits the upstream and downstream beams to be sharply focused on the oil film surface. One beam passes through a half-wave retardation plute to rotate its polarization 90° before it reaches the oil film. The beams reflected from the oil film and the model surface are separated by a polarization beam splitter and focused on photodetectors. The light intensity signals from the photodetectors are recorded. The transmitting and receiving optics are mounted on platforms removed from the wind tunnel. As the air flow in the wind tunnel spreads the oil film and changes its thickness, alternate constructive and destructive interferences are produced by the beam reflections from the oil and the model surface. These interferences modulate the light intensity reaching each photodetector. Each crest on a recorded light intensity trace represents an oil thickness corresponding to maximum constructive interference between the reflections (phase coincidence). By counting the number of fringes over a given time span, the resulting change in oil thickness can be precisely determined in terms of the known laser wavelength. With this information and other known constants, the skin friction of the model may be calculated from equations provided.

An advantage of the invention is that it does not interfere with the air flow over the model. The use of two measurement laser beams obviates the need to locate the leading edge of the oil film. Accordingly, the measurement process is accelerated and errors are eliminated. The mounting of the laser transmitter and receiver on separate platforms such as portable optical tripods eliminates the detrimental effects of wind tunnel vibration on the skin friction measurements. It also allows quick and versatile repositioning of the interferometer to any location in the wind tunnel where optical access is provided for the light beams. Another salient feature of this invention is that one may select desired time periods from the recorded data. One is not required to measure the total time that the oil flows. This eliminates errors resulting from prerum oil flow, tunnel starting transients, and initial surface waves on the oil film.

BRIEF DESCRIPTION OF DRAWINGS

With reference to the accompanying drawings.

DETAILED DESCRIPTION OF THE INVENTION

Figure 1:
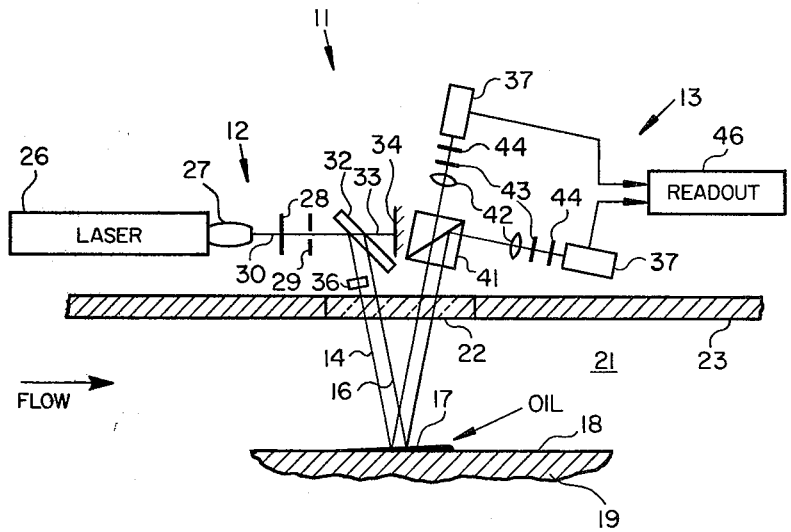
FIG. 1 is a schematic diagram of a preferred dual-beam skin friction interferometer in accordance with the invention.

Referring to FIG. 1, a dual-beam laser skin friction interferometer 11 constructed in accordance with the invention comprises a laser transmitter 12 and a laser receiver 13. Laser transmitter 12 produces two laser beams 14, 16 that are focused at arbitrary points on an oil film 17 applied to the surface 18 of a test object 19. The interferometer 11 measures the rate of change in thickness of the flowing oil film 17 at two points just behind the leading edge of the film. Test object 19, for example a wing or a scale model of a wing, is secured within wind tunnel 21 by a sting or other conventional apparatus (not shown). Laser beams 14 and 16 pass through a window 22 in wall 23 of wind tunnel 21 before reaching oil film 17.

Laser transmitter 12 includes a low power linearly polarized laser 26 such as an He-Ne laser. The beam from the laser is first passed through a beam expanding variable-focal-length telescope 27, a neutral density filter 28 and an iris diaphragm 29 before being divided into two parallel beams 14, 16 by an angled interferometer flat 32. Neutral density filter 28 reduces the power level of beam 30 to a value that avoids excessive heating of oil 17. The reflections from the sides of the flat provide two exactly parallel equal-intensity beams with a spacing that can be accurately computed from the known properties of the flat. Radiation 33 passing through interferometer flat 32 impinges on an optical stop 34. The iris diaphragm 29 is stopped down so that beams 14 and 16 do not overlap. Beam 14 is passed through a half-wave retardation plate 36 to rotate its polarization 90° from beam 16. The two beams pass through window 22 and are point focused on oil film 17 by adjusting the focus of telescope 27. The elements of laser transmitter 12, namely laser 26, telescope 27, filter 28, iris diaphragm 29, flat 32 and half-wave retardation plate 36, are commonly mounted on a base (not shown), such as a portable optical tripod, separate from wind tunnel 21 so that the transmitter will be isolated from detrimental tunnel vibrations.

The two reflected beams coming from the oil-wetted surface of test object 19 are first passed through a polarization beam splitter 41 of laser receiver 13 to separate the beams according to their polarization. Each beam emanating from splitter 41 is focused by a lens 42 onto a light detector 37 which generates a signal represenative of the intensity of light impinging thereon. The signals from detectors 37 are conveyed to readout 46 which is preferably a recording device such as a dual-channel strip chart recorder. A polarizer 43 and a narrow-band interference filter 44 are positioned in front of each light detector 37 to provide noise reduction. The elements of the laser receiver 13, with or without readout 46, are all mounted on a base (not shown), for example a portable tripod, apart from the wind tunnel 21 and the laser transmitter 12. The light intensity records for the two beams are then used to derive skin friction according to the procedure set forth below.

Figure 3:
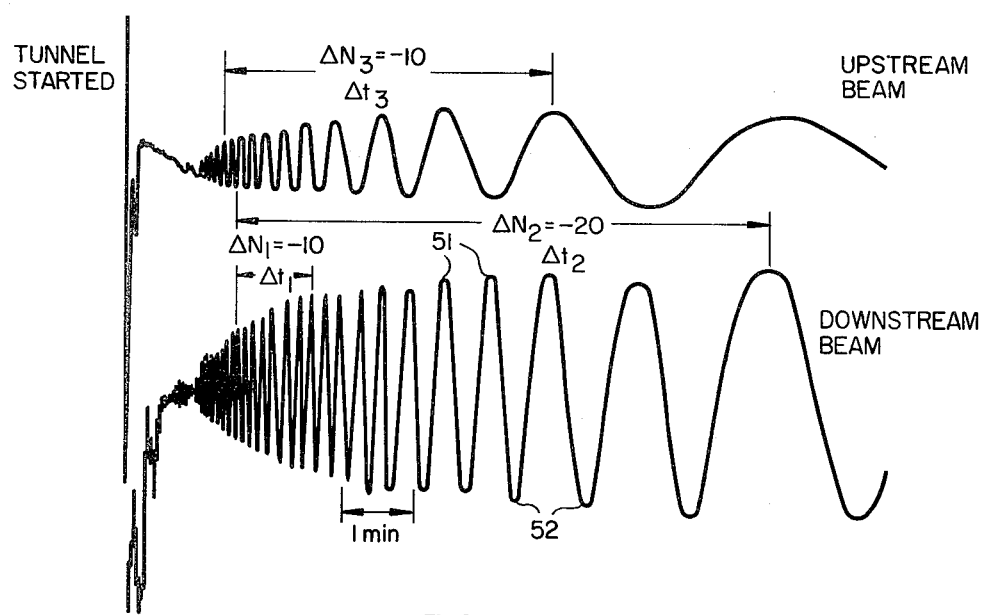
FIG. 3 depicts a typical interferometer fringe record resulting from the operation of the apparatus in FIG. 1.

A typical output record from dual-beam interferometer 11 is depicted in FIG. 3. The upper waveform is representative of the light reflected from oil film 17 and test object 19 by beam 14 whereas the lower waveform is representative of the light reflected from film 17 and test object 19 by beam 16. The ordinate represents light intensity and the abcissa depicits time. As time elapses, the thickness of oil film 17 diminishes and diminishes non-linearly. Crests 51 symbolize points of maximum constructive interference between reflections (from the surface of oil film 17 and surface 18 of test object 19) whereas troughs 52 represent points of maximum destructive interference between reflections. At crests 51 the reflections are exactly in phase and at troughs 52 the reflections are 180° apart. After the tunnel is started and air flows over the film 17, each light detector 37 sees interference fringes passing before it. As will be pointed out in detail later, the skin friction of test object 19 can be determined by referring to the recorded outputs of photodetectors 37 and counting the fringes occurring in a selected period. The fringes seen by a light detector 37 during period P are a function of the crests (or troughs) produced during the period P. The erratic behavior of the waveforms, in FIG. 3, just after the tunnel is started is a result of transient waves in the oil. Fringes should be counted after the transient waves have subsided and the oil has thinned enough so that there is a discernible displacement between adjacent crests. At the very beginning of a test, resolution is improved as the beam diameter is lessened. During period $\Delta t_1$, 10 fringes pass before the photodetector 37 associated with the downstream beam 16. Although period $\Delta t_2$ is over three times larger than period $\Delta t_1$, it is noted that only 20 fringes pass by photodetector 37. This clearly demonstrates how the oil film thickness diminishes non-linearly with time.

The procedure for deriving skin friction from the recorded interferometer data is set forth below. The density of oil film 17, the oil index of refraction, the laser wavelength, and the oil kinematic viscosity are constants that must be known for the derivation. The following terms are utilized in the explanation of the procedure.

Nomenclature $C_i$ = coefficients in Eqs. (24) to (32)
$c_f$ = local skin friction coefficient, $\tau/q$
$dp/dx$ = external flow pressure gradient
$G$ = oil viscosity function
$g$ = gravitational acceleration I = incidence angle for interferometer flat
i = incidence angle for oil
N = fringe number
$n_g$ = interferometer flat index of refraction
$n_o$ = oil index of refraction
q = free-stream dynamic pressure
R = refraction angle for interferometer flat
r = refraction angle for oil
T = interferometer flat thickness
t = time
x = distance from oil film leading edge
$x_s$ = distance correction for surface tension
y = oil thickness
α+ initial oil film leading-edge slope
ΔN = incremental change in fringe number
Δt = incremental change in time
Δx = beam spacing
δ = fixed oil sublayer thickness on a surface
ε = pressure gradient and gravity correction parameter
Θ = surface inclination from horizontal
λ = laser wavelength
θ = oil kinematic viscosity
ρ = oil density
τ = local skin friction Superscripts ( )' = corrected or "effective" value
$\overline{(\ )}$ = average value The above-cited Tanner and Blows reference shows that an oil film on a surface subject to a constant shear stress will assume the linear shape $$x = \tau y t / \rho \theta \quad (1)$$

In the other cited Tanner papers, the author observed that a very small layer of oil, with a thickness δ of the order of a few nanometers, will always stick to a surface without flowing. Taking into account a finite initial leading-edge slope α to approximately account for any prerun oil flow and that the effect of leading-edge surface tension is unimportant for the case of skin friction acting on oil, Eq. (1) may be written as:

$$x = \frac{\tau(y - \delta)t}{\rho v} + \alpha^{-1}(y - \delta) \quad (2)$$

Relating the thickness of the oil film 17 to the wavelength λ of the laser interferometer beam, the quantity y can be expressed in terms of the fringe number N by $$N\lambda = 2 n_o y \cos(r) \quad (3)$$

where $$\cos(r) = \cos\left[\arcsin\left(\frac{\sin(i)}{n_o}\right)\right] \quad (4)$$

By this definition, N assumes integer values for oil thicknesses corresponding to reflected beam maximum constructive interferences. N', the corrected or effective fringe number, and t', the corrected or effective oil-flow time are defined as follows:

$$N' = N - \frac{2 n_o \delta \cos(r)}{\lambda} \quad (5)$$

-continued $$t' = t + \frac{\rho v}{\alpha \tau} \quad (6)$$

Figure 2:
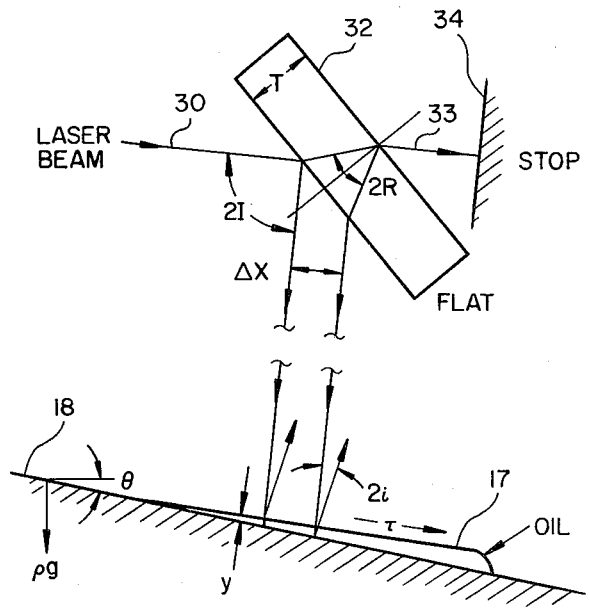
FIG. 2 is a much enlarged diagrammatic representation of the interferometer flat and the oil film on the model.

Using the notation shown in FIGS. 2 and 3, skin friction may then be written as $$\tau = \frac{2 n_o \rho v \cos(r)}{\lambda} \frac{\Delta x}{\Delta(N't')} = \frac{2 n_o \rho v \cos(r)}{\lambda} \frac{\Delta x}{(N_1' t_1' - N_2' t_2')} \quad (7)$$

Equating the product N't' at different arbitrary times on each interferometer waveform (FIG. 3) one obtains $$N_1 = -\Delta N_1 \cdot \frac{\frac{\Delta N_2}{\Delta N_1}\left(\frac{\Delta t_2}{\Delta t_1} - 1\right)}{\left(\frac{\Delta t_2}{\Delta t_1} - \frac{\Delta N_2}{\Delta N_1}\right)} \quad (8)$$

$$t_1' = -\Delta t_1 \cdot \left(\frac{N_1}{\Delta N_1} + 1\right) \quad (9)$$

and $$N_2 = -\Delta N_3 \cdot \left(\frac{t_2'}{\Delta t_3} + 1\right) \quad (10)$$

Herein, effective time t' begins after the wind tunnel is started and the onset transient waves subside in the oil film. The time when t'=0 cannot be observed from the recorded data. Of course once a particular t' is determined on the waveforms, the effective time of any other trace point can be measured. The necessary effective time calibration is provided by Eq. (9). $t_1'$ is defined as the beginning of $\Delta t_1$ and $\Delta t_2$ whereas Period $\Delta t_3$ begins at $t_2'$. The selection of $t_1'$ and $t_2'$ from the recorded waveforms is a matter of choice as is the length of periods $\Delta t_1$, $\Delta t_2$ and $\Delta t_3$ (however, $\Delta t_1$ and $\Delta t_2$ must begin at the same time). So once Eq. (9) is solved and $t_1'$ is known, $t_2'$ can be determined directly from FIG. 3 by measuring the x coordinate distance between the beginning of $\Delta t_1$ and $\Delta t_3$. If, for example, $t_1'$ is 58 seconds, the recording medium moves ½ inch/minute and the distance between the beginning of $\Delta t_1$ and $\Delta t_3$ is ⅛ inch, then the recording medium would move ⅛ inch in 15 seconds and $$t_2' = (t_1' - 15) \text{ seconds}$$
$$= (58 - 15) \text{ seconds}$$
$$= 43 \text{ seconds}$$

The beam spacing Δx can be either measured or computed from geometric optics (see FIG. 2 for notation)

$$\Delta x = 2T \cos(I) \cdot \tan(R) \quad (11)$$

where $$\tan(R) = \tan\left[\arcsin\left(\frac{\sin(I)}{n_g}\right)\right] \quad (12)$$

With Δx known, Eq. (7) is solved for τ, skin friction.

If the surface 18 supporting the oil 17 is not horizontal and has an angle Θ (FIG. 2), a gravity force will act on the oil together with the shear stress. If the effect of gravity force or an external flow pressure gradient is small compared to the effect of the shear stress the forces may be accounted for by this approximation $$\tau' = (1-\epsilon)^{-1}\tau \quad (13)$$

where $$\epsilon = \left[\tfrac{1}{3}\frac{y}{\tau} + \tfrac{2}{3}\frac{\rho v x}{\tau^2 t}\right] \cdot \left[\frac{dp}{dx} - \rho g \sin(\theta)\right] \quad (14)$$

Eq. (14) may be further simplified by assuming that the shear stress within the bracket is the uncorrected value, setting y equal to $y_1$ (the thickness of the oil at the downstream beam), and introducing the fringe number through Eq. (3) for this result $$\epsilon \simeq \frac{\lambda N'_1}{2n_o \tau \cos(r)} \left[\frac{dp}{dx} - \rho g \sin(\theta)\right] \quad (15)$$

If the kinematic viscosity of the oil film is not known, the dual-beam interferometer 11 may be utilized to measure it. In the case of a viscosity measurement by interferometer 11, no air motion is relied on to cause flow of oil film 17. Surface 18 is inclined to angle Θ (up to 90°) and gravity is solely relied on to cause flow of oil 17 (see FIG. 2). Of course the area of the surface 18 under oil 17 must be reflective of light at the laser wavelength. In some instances it may be necessary to polish the area to make it a suitable light reflector. When gravity is the only force acting on the oil film it will assume the parabolic shape $$x = \frac{y^2 t g \sin(\theta)}{v} \quad (16)$$

Introducing δ and α as was previously done, and bringing in a correction for x for the effect of surface tension near the film leading edge $x_s$ results in Eq. (16) becoming $$x = \frac{(y-\delta)^2 t g \sin(\theta)}{v} + \alpha^{-1}(y-\delta) + x_s \quad (17)$$

Then, taking the fringe number from Eq. (13) and using the definition of effective fringe number from Eq. (5) it is possible to define a viscosity function G as $$G = \frac{\lambda^2 g \sin(\theta)}{4v\, n_o^2 \cos^2(r)} \quad (18)$$

Equation (17) then becomes $$x - x_s = GN'^2 \left[t + \frac{2v n_o \cos(r)}{a\lambda g \sin(\theta) N'}\right] \quad (19)$$

By assuming that the incremental changes in N' for any set of measurements from the interferometer records are small compared to N' itself (and this can be insured by taking the measurements over a small time interval), an effective distance and time can be defined, respectively, as $$x' \simeq x - \bar{x}_s \quad (20)$$

and $$t' \simeq t + \frac{2v n_o \cos(r)}{a\lambda g \sin(\theta) \bar{N}'} \quad (21)$$

where $\bar{x}_s$ and $\bar{N}'$ are average values during a measurement time interval. With these definitions then Eq. (19) now becomes $$x' = GN'^2 t' \quad (22)$$

and a version taking into account the displacement of the beams and the data from the interferometer traces (FIG. 3) may be written as $$G = \frac{\Delta x}{\Delta(N'^2 t')} = \frac{\Delta x}{(N'^2_1 t'_1 - N'^2_2 t'_2)} \quad (23)$$

To solve for the N's and t's, it is possible to take advantage of the fact that product $N'^2 t'$ is constant for fixed x' (Eq. 22). Employing an analysis similar to a previous one for shear stress, a cubic equation for $N'_1$ evolves as $$N'^3_1 + \frac{C_2}{C_1} N'^2_1 + \frac{C_3}{C_1} N'_1 + \frac{C_4}{C_1} = 0 \quad (24)$$

where $$C_1 = 2 \cdot \left[\frac{\Delta t_2}{\Delta t_1} - \frac{\Delta N_2}{\Delta N_1}\right] \quad (25)$$

$$C_2 = \Delta N_1 \cdot \left[4 \cdot \frac{\Delta N_2}{\Delta N_1} \cdot \left(\frac{\Delta t_2}{\Delta t_1} - 1\right) + \frac{\Delta t_2}{\Delta t_1} - \left(\frac{\Delta N_2}{\Delta N_1}\right)^2\right] \quad (26)$$

$$C_3 = 2\Delta N_1 \cdot \Delta N_2 \cdot \left[\left(\frac{\Delta N_2}{\Delta N_1} + 1\right) \cdot \left(\frac{\Delta t_2}{\Delta t_1} - 1\right)\right] \quad (27)$$

and $$C_4 = \Delta N_1 \cdot (\Delta N_2)^2 \cdot \left[\frac{\Delta t_2}{\Delta t_1} - 1\right] \quad (28)$$

Also, $$t'_1 = -\Delta t_1 \left[\frac{\left(\frac{N'_1}{\Delta N_1} + 1\right)^2}{\left(2 \cdot \frac{N'_1}{\Delta N_1} + 1\right)}\right] \quad (29)$$

and $$N'^2_2 + C_5 N'_2 + C_6 = 0 \quad (30)$$

where $$C_5 = 2 \cdot \Delta N_3 \cdot \left(\frac{t'_2}{\Delta t_3} + 1\right) \quad (31)$$

and

-continued $$C_6 = (\Delta N_3)^2 \cdot \left(\frac{t'_2}{\Delta t_3} + 1\right) \quad (32)$$

Finally, the oil kinematic viscosity is arrived at by combining Eqs. (18) and (23)

$$\nu = \frac{\lambda^2 g \sin(\theta)}{4 n_o^2 \cos^2(r)} \cdot \left[\frac{(N'_1{}^2 t_1 - N'_2{}^2 t'_2)}{\Delta x}\right] \quad (33)$$

Figure 4:
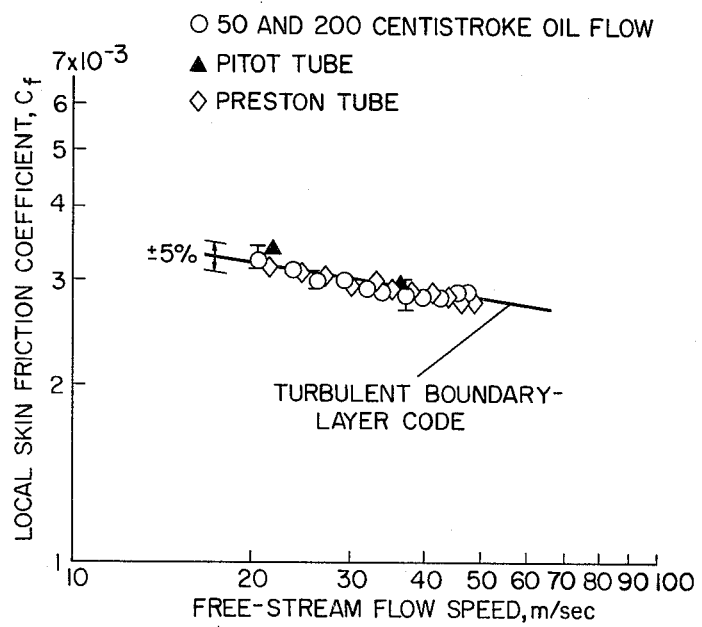
FIG. 4 is a graph providing a comparison of skin friction measurements.

A dual-laser-beam interferometer for measuring skin friction in wind tunnels by monitoring the thickness change of an oil film at two points has been described. It allows nonintrusive measurement of skin friction in many complex flows where other techniques are limited or impractical, and it eliminates the error-introducing need to measure the distance to the oil leading edge and the starting time for the oil flow. The accuracy of the interferometer has been well established by extensive comparisons with results of conventional skin friction measurements and with predictions based on turbulent boundary-layer theory. In FIG. 4 the circles represent skin friction measurements made with the instant invention (for two different oil viscosities). As indicated, measurements were also made with a Preston tube and a pitot tube. In the latter instance skin friction from the mean velocity profiles was obtained by plotting the data on a Clauser chart to fit the "law-of-the-wall" as described by D. Coles, "The Young Person's Guide to the Data," Proceedings AFOSR-IFP-Stanford Conference on Computation of Turbulent Boundary Layers, Department of Mechanical Engineering, Stanford University, 1968. The turbulent boundary layer code employed is the one mentioned in "Progress in Turbulence Modeling for Complex Flowfields, Including Effects of Compressibility," D. C. Wilcox and M. W. Rubesin, NASA TP-1517, 1980. The three different measurements schemes and the prediction and within 5% of each other.

I claim:

1. Apparatus for measuring the thickness change of an oil film on a light reflective surface while said oil film is flowing comprising:
   means for fixedly directing first and second parallel coherent light beams of a known wavelength on said oil film at points A and B, respectively, for reflection by said oil film and said surface adjacent thereto, said beams being a known distance apart and said first beam being upstream from said second beam;
   means for rotating the plane of polarization of said first beam 90° with respect to the plane of polarization of said second beam;
   means for separating the two beams reflected from said oil film and said surface into paths normal to each other,
   light detection means interposed in each path for generating a signal representative of the beam intensity, and
   means for recording each signal so that the frequency of interference fringes at said points A and B may be determined.

2. The apparatus of claim 1 wherein said means for directing said first and second coherent light beams comprises a laser and an interferometer flat.

3. The apparatus of claim 1 wherein said oil film and surface are situated within a wind tunnel and said oil film is caused to flow by the air movement within said wind tunnel.

4. Apparatus for measuring the thickness change of an oil film on a light reflective surface while said oil film is flowing comprising:
   laser means for generating a coherent light beam,
   an interferometer flat fixedly and obliquely interposed in said beam and producing first and second parallel beams impinging on and reflecting from said oil film and said surface adjacent thereto, said first beam being upstream of said second beam and said first and second beams impinging on said oil film at points A and B;
   a half-wave retardation plate stationed between said interferometer flat and said oil and interposed in said first beam to rotate its polarization by 90°;
   a polarization beam splitter situated to receive said beams reflected from said oil film and separate them into two paths orthogonal to each other;
   first and second light detectors each adapted to generate a signal representative of the light intensity received;
   means for focusing the two beams emanating from said polarization beam splitter onto said light detectors, respectively;
   and means for recording each light detector signal whereby the interference fringes occurring at points A and B as the oil film thickness changes may be determined.

5. Apparatus as set forth in claim 4 wherein said focusing means includes polarizers and interference filters to reduce noise at each light detector.

6. Apparatus as set forth in claim 5 wherein said oil film is located on the surface of a test object in a wind tunnel and said first and second beams and their reflections from said oil film and surface are transmitted through a window of said wind tunnel.

7. Apparatus for measuring data useful for a skin friction calculation comprising:
   a wind tunnel with a window;
   a test object with a light reflective surface situated within said tunnel in proximity to said window;
   an oil film located on said surface and adapted to flow and change thickness when subjected to the shear stress of the air flow within said tunnel;
   a laser transmitter positioned outside of said wind tunnel and capable of directing first and second light beams through said window onto said oil film at points A and B a known distance apart, said first beam being upstream of said second beam;
   a laser receiver positioned outside of said wind tunnel and adapted to receive the two light beams reflected from the oil film and the test object surface thereunder, said laser receiver including means for separating the two reflected beams and focusing them on separate light detectors, said detectors generating signals representative of the interference fringes at points A and B, respectively; and
   means coupled to said light detectors for recording said signals.

8. Apparatus as set forth in claim 7 wherein said laser transmitter includes a laser, an interferometer flat and a half-wave retardation plate, said interferometer flat being interposed obliquely in the light path of said laser whereby two parallel light beams are reflected from said flat, said half-wave retardation plate being interposed in the path of one of the reflected beams to rotate its polarization by 90°.

* * * * *